United States Patent [19]
Hurwitz

[11] Patent Number: 5,662,605
[45] Date of Patent: Sep. 2, 1997

[54] EAR IRRIGATION DEVICE AND METHOD

[76] Inventor: Stanley Hurwitz, 5600 Williams Road, Richmond, British Columbia, Canada, V7E 1K3

[21] Appl. No.: 562,569

[22] Filed: Nov. 24, 1995

[51] Int. Cl.$^6$ .................................................. A61M 31/00
[52] U.S. Cl. ..................... 604/54; 604/73; 604/118; 604/150; 604/151; 601/160
[58] Field of Search ..................... 601/161, 162, 601/160; 604/30, 31, 48, 49, 246, 257, 289, 290, 54, 73, 77, 118, 150, 151, 275

[56] References Cited

U.S. PATENT DOCUMENTS

| | | | |
|---|---|---|---|
| 4,607,627 | 8/1986 | Leber et al. | 601/161 |
| 5,309,899 | 5/1994 | Ginsberg | 604/38 |
| 5,344,317 | 9/1994 | Pacher et al. | 601/162 |
| 5,389,078 | 2/1995 | Zalesky et al. | |
| 5,527,275 | 6/1996 | Ginsberg | |

*Primary Examiner*—Mark Bockelman
*Attorney, Agent, or Firm*—Long and Cameron

[57] ABSTRACT

An ear irrigation device has a pump communicating with a water container for pumping water through a tube to a handpiece nozzle, for discharge into a person's ear. A control circuit operated by a switch energizes a motor, for driving the pump. The control circuit generates pulses to intermittently energize the motor, and the pulses are automatically controlled so as to positively restrict pressure discharge of water from the nozzle to a low pressure on actuation of the switch and subsequently to permit an increase in the pressure of the water discharge only after a predetermined time interval.

5 Claims, 2 Drawing Sheets

EAR IRRIGATION DEVICE AND METHOD

BACKGROUND OF THE INVENTION

1. Field of the Invention

The present invention relates to an ear irrigation device and to a method of irrigating a person's ear and, more particularly, is concerned with a device and method for discharging water from a nozzle into a person's ear.

2. Description of the Related Art

In U.S. Pat. No. 5,309,899, issued May 10, 1994 to Irwin A. Ginsberg, there is disclosed a system for cleansing a patient's ear which has a portable applicator comprising a hand piece and a nozzle for insertion into the patient's ear for discharging a flow of liquid into the ear, a control unit provided with a heater, and a controller for maintaining the temperature of the liquid within certain limits and for limiting the pressure of the liquid and varying the flow rate of the liquid.

The control unit varies a flow rate signal to solenoid valves controlling the flow output of a pump to the nozzle. More particularly, the control unit receives an output signal from a potentiometer in the handpiece, in response to manual displacement of a plunger. The control unit then generates an appropriate command to the solenoid valves, which will open to provide a controlled pressure flow and flow-rate and, further, can operate in rhythmic fashion to provide a pulsing flow to the handpiece.

It is a disadvantage of this prior system that the pressure and flow rate are controlled by the mount of manual displacement of the plunger and may therefore inadvertently be caused to be excessive, at the start of the ear irrigation, by undue displacement of the plunger.

The present invention is based on an appreciation of the fact that the ear drum of a person's ear is normally in a relaxed state. However, when the ear drum is impinged by a pressure, for example a loud soundwave, the ear drum automatically tightens. It is not only uncomfortable, but also dangerous, to impinge the ear drum, while it is in its relaxed state, by a relatively high pressure.

SUMMARY OF THE INVENTION

It is accordingly an object of the present invention to provide a novel, mechanically simplified and improved ear irrigation device which not only varies the pressure at which water is discharged from a nozzle into a person's ear, but which in addition positively prevents an initial discharge of water at high pressure and ensures that, upon actuation of a switch to initiate the ear irrigation, the water is discharged at only at a low pressure, for an initial period of time, to allow the person's ear drum to tighten without discomfort.

According to the present invention, there is provided an ear irrigation device which comprises a pump communicating with a water container and with a tube for pumping water from the water container through the tube and through a nozzle connected to the tube into the ear of a person. A control circuit, which is connected to a switch for energizing the pump, energizes the motor in response to actuation of the switch. The control circuit includes means for automatically limiting the energization of the motor so as to provide an initial low pressure discharge of water from the nozzle on actuation of the switch and for subsequently permitting an increase in the pressure of the water discharge only after a predetermined time interval.

In a preferred embodiment of the invention, the nozzle and the switch are provided at a free end of the tube and a conductor extends along and within the tube for connecting the switch to the control circuit.

In this embodiment, the control circuit includes means which are adjustable for variably presetting the pressure of the water discharge.

Also according to the present invention, there is provided a method of irrigating a person's ear which comprises inserting a nozzle into the ear, pumping water through the nozzle into the ear and automatically limiting the pressure of the water discharged from the nozzle into the ear for a predetermined time so that the pressure is initially at a low pressure, to avoid discomfort to the patient, and subsequently increasing the pressure.

BRIEF DESCRIPTION OF THE DRAWINGS

The invention will be more readily understood from the following description thereof when taken in conjunction with the accompanying drawings, in which.

DESCRIPTION OF THE PREFERRED EMBODIMENT

Figure 1:
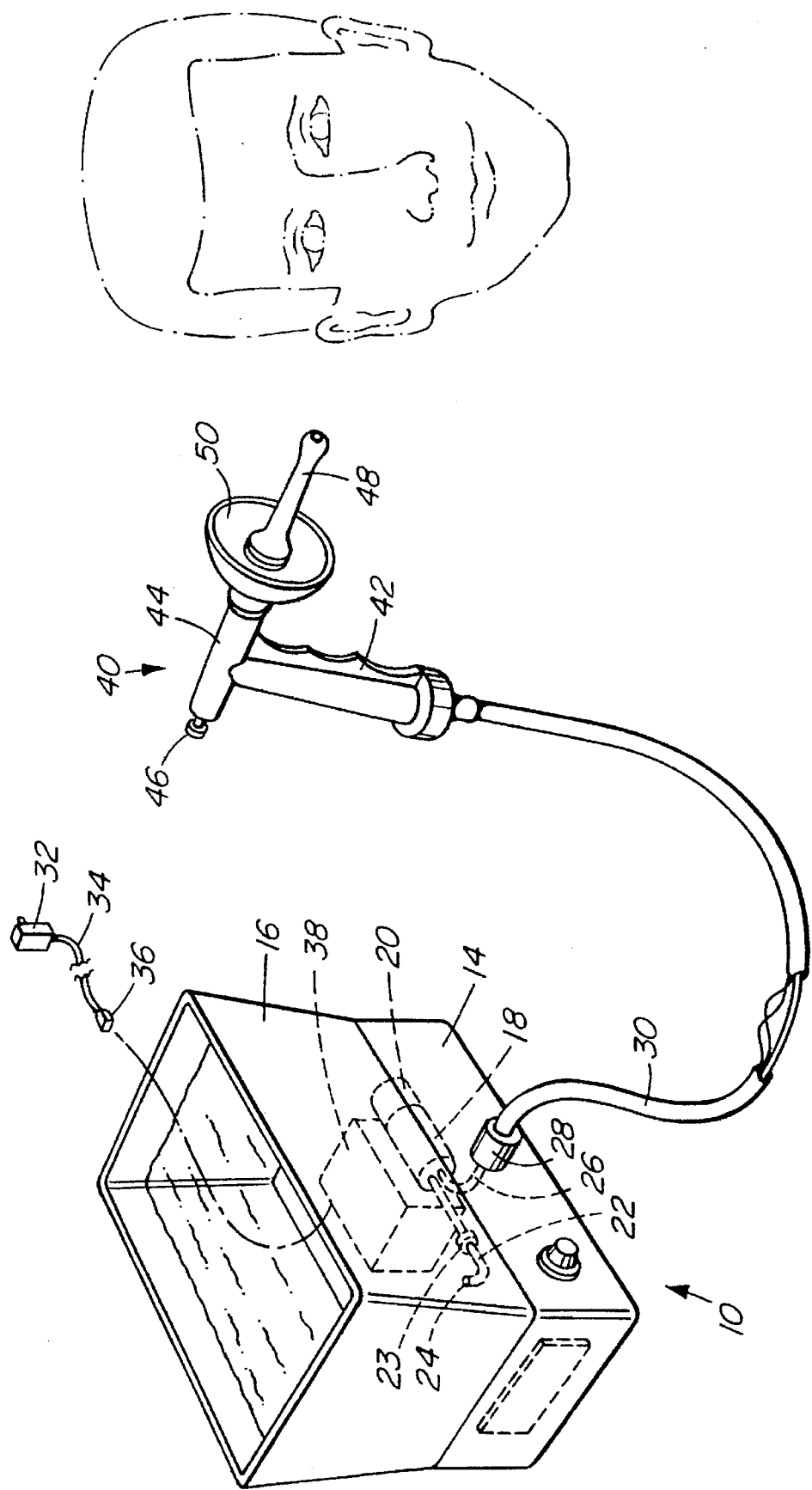
FIG. 1 shows a view in perspective of an ear irrigation device according to the present invention.

In FIG. 1 of the accompanying drawings, reference numeral 10 indicates generally an ear irrigation device for irrigating the ear of a person.

The ear irrigation device 10 has a lower housing 14, on the top of which there is mounted an upwardly-open water container 16. The housing 14 contains a water pump 18, with an associated electric motor 20 for driving the pump 18. The pump 18 has an inlet pipe 22, which is provided with a one-way valve 23 and which communicates with the interior of the water container 16 through an opening 24 in the bottom of the latter, and a water outlet pipe 26, which is connected through a covering 28 to a flexible tube 30, so that water drawn into the pump 18 through the water inlet pipe 22, during operation of the pump 18, is pumped through the water outlet pipe 26 to the tube 30.

A wall plug 32, for insertion into a wall socket (not shown), is connected by a conductor 34 to a connector 36, which is releasably insertable into a control unit 38 for energizing the latter and the electric motor 20. The connector 36 must be disconnected from the control unit 38 in order to render the device 10 operational, as described below.

The flexible tube 30 is connected, at a free end thereof, to a hand-piece indicated generally by reference numeral 40, which comprises a hand grip 42 provided with a cylindrical body 44. At one end of the cylindrical body 44, there is provided an actuating knob 46. A nozzle 48, in the form of an ear syringe, is provided at the opposite end of the cylindrical body 44 and projects from a semi-spherical cup 50. The cup 50 serves, in known manner, to reduce splashing when the nozzle 48 is in use for discharging a flow of water into an ear.

Figure 2:
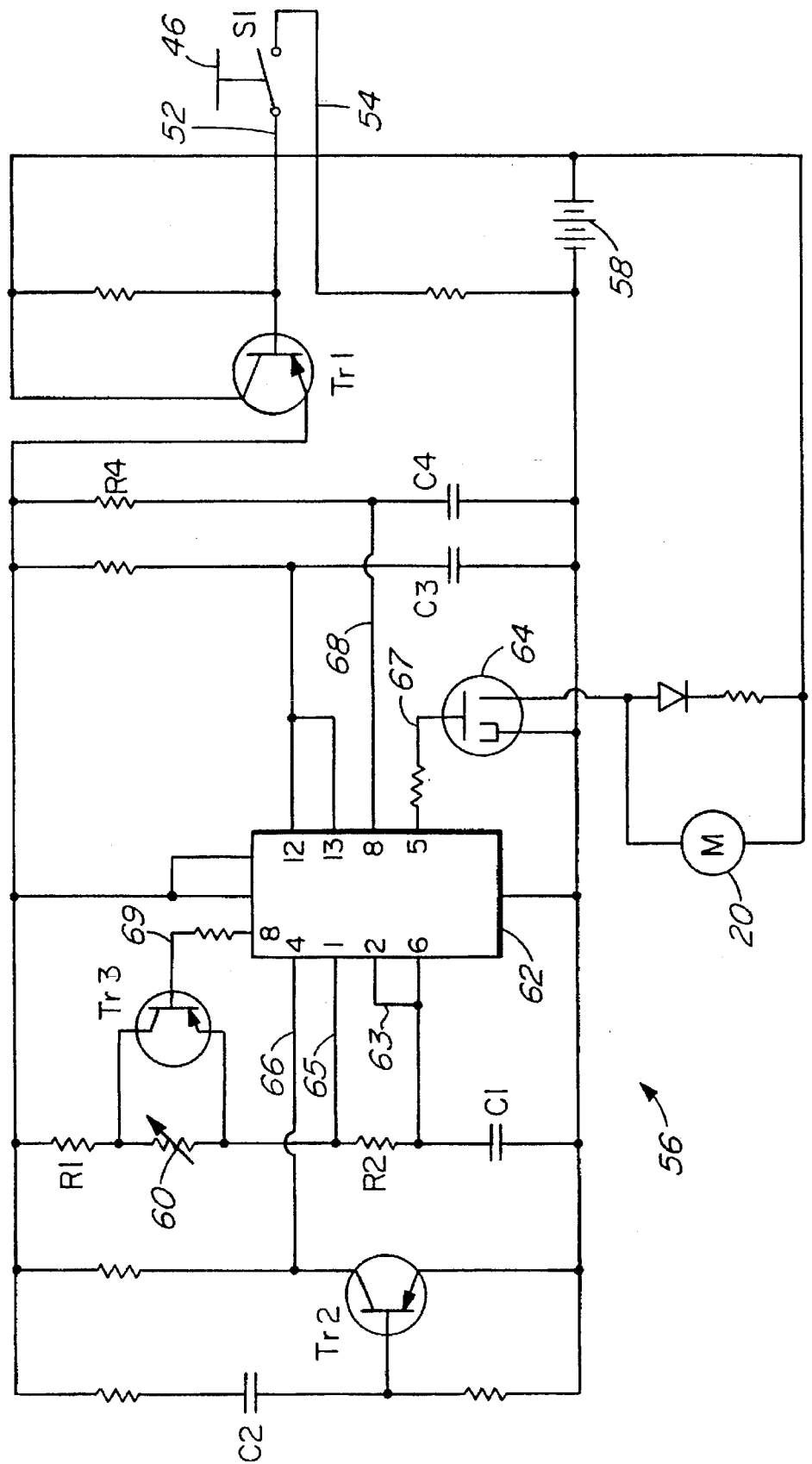
FIG. 2 shows a circuit diagram of a control circuit included in the device of FIG. 1.

The actuating knob 46 is provided for closing a normally-open switch S1 (FIG. 2) connected between conductors 52 and 54 which, as shown by a broken-away portion of the tube 30 in FIG. 1, extend along the interior of the tube 30. The conductors 52 and 54 thus connect the switch S1 to a control circuit indicated generally by reference numeral 56 in FIG. 2, which is provided in the control unit 38 of FIG. 1.

More particularly, the conductor 52 is connected to the base of a transistor Tr1, which serves as a switch for controlling the energization of the control circuit 56 from a rechargeable battery 58. The battery 58 can be charged through the wall plug 32, and the connector 36 can then be disconnected from the control unit 38, so that the ear irrigation device 10 can be operated solely by the energy of the battery 58, thus avoiding risk of electrocution of the patient 12.

The control circuit 56 includes a further transistor Tr2 for ensuring that no pulse occurs when the switch S1 is initially closed, and a transistor Tr3 provided with a potentiometer 60 which is adjustable for controlling the operation of a timer 62. The timer 62, which in the present embodiment is a commercially available dual timer marketed as a Model 556 dual timer by Tandy Inc., provides pulses to an electronic switch 64 for energizing the motor 20 and thereby operating the pump 18 to deliver a discharge of water from the nozzle 48. The transistor Tr3 serves to short-out the potentiometer 60 for a predetermined period of time, on closure of the switch S1, and thereby ensures that the water discharge from the nozzle 48 is initially at a low pressure.

When the switch S1 is initially closed, by actuation of the knob 46 in the handpiece 40, the motor 20 is energized so as to deliver the water discharge from the nozzle 48 at a low pressure. After a period of, in the present embodiment, three seconds, the energization of the motor 20 is increased, to a rate preset by adjustment of the potentiometer 60, so as to increase the pressure of the water discharge from the nozzle 48 to a pre-determined corresponding preset level.

More particularly, the transistor TR1 acts as a switch and, on closure of the switch S1, is negatively biased to apply a voltage to the timer 62. The timer 62 has threshold and trigger pins 2 and 6 connected by a conductor 63 and therefore functions as an oscillator. Capacitor C1 is charged via resistors R1 and R2 and the potentiometer 60, but discharges through resistor R2 and conductor 65 to pin 1 of the timer 62. The oscillator frequency is independent of the voltage on conductor 63 but is controlled by the adjustment of the potentiometer.

The transistor Tr2, through conductor 66, holds reset pin 4 of the timer 62 negative at the start of the operation. The capacitor C2 determines the duration of the reset cycle, and ensures that an output from the timer 62 to the switch 64 on conductor 67 remains low for an initial period, typically ½ second, after the initial closure of the switch S1. The switch 64 is a MOSFET, which pulses the motor 20.

Through resistor R4 and conductor 68, a voltage is applied to a trigger pin 8 of the timer 62 on closure of the switch S1. Capacitor C4 prevents spurious pulses. An output from the timer 62 on conductor 69 then goes low, causing the transistor Tr3 to short out the potentiometer 60 at start-up, thus allowing a rapid charge/discharge cycle at start-up.

When the switch S1 is subsequently again opened, by release of the actuating knob 46, the control circuit 56 is reset.

I claim:

1. An ear irrigation device, comprising:

an electric motor;

a control switch;

a control circuit responsive to actuation of said switch to provide a control signal for energizing said electric motor;

said control circuit including timing means for automatically varying said control signal after a predetermined interval of time following the actuation of said control switch to increase the speed of said electric motor;

a water container;

a nozzle for insertion in a person's ear;

a tube connected to said water container and said nozzle and a pump communicating with said water container and, through said tube, with said nozzle and connected to said electric motor for pumping water from said water container to said nozzle at a pressure which increases with increased motor speed.

2. An ear irrigation device as claimed in claim 1, wherein said timing means include means for adjusting the duration of the predetermined interval of time.

3. An ear irrigation device as claimed in claim 1, further comprising a conductor extending along said tube and connecting said switch to said control circuit, said tube being connected at one end thereof to said water container; and said switch and said nozzle being provided at an opposite, free end of said tube.

4. A method of irrigating a person's ear, which comprises the steps of inserting a nozzle into the ear, discharging water via said pump through the nozzle into the ear at an initial low water discharge pressure to counteract discomfort to the patient, timing the discharge of the water from the nozzle via a control circuit and said control circuit automatically effecting an increase in the water discharge pressure via said pump after a predetermined interval of time.

5. A method as claimed in claim 4, which includes adjusting the duration of the predetermined interval of time.

* * * * *